United States Patent
Kashima et al.

(10) Patent No.: US 12,114,833 B2
(45) Date of Patent: Oct. 15, 2024

(54) OPTICAL SYSTEM, ENDOSCOPE, AND MEDICAL IMAGE PROCESSING SYSTEM

(71) Applicant: SONY GROUP CORPORATION, Tokyo (JP)

(72) Inventors: Koji Kashima, Tokyo (JP); Takeshi Miyai, Tokyo (JP); Junichiro Enoki, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 223 days.

(21) Appl. No.: 17/440,217

(22) PCT Filed: Mar. 16, 2020

(86) PCT No.: PCT/JP2020/011448
§ 371 (c)(1),
(2) Date: Sep. 17, 2021

(87) PCT Pub. No.: WO2020/196027
PCT Pub. Date: Oct. 1, 2020

(65) Prior Publication Data
US 2022/0142458 A1    May 12, 2022

(30) Foreign Application Priority Data
Mar. 28, 2019  (JP) .................. 2019-063267

(51) Int. Cl.
*H04N 23/56* (2023.01)
*A61B 1/00* (2006.01)
(Continued)

(52) U.S. Cl.
CPC ........ *A61B 1/000095* (2022.02); *A61B 1/042* (2013.01); *A61B 1/045* (2013.01);
(Continued)

(58) Field of Classification Search
CPC ... A61B 1/000095; A61B 1/042; A61B 1/045; A61B 1/0669; A61B 1/07; H04N 23/56;
(Continued)

(56) References Cited

U.S. PATENT DOCUMENTS 9,055,248 B2 * 6/2015 Atif ...................... H04N 25/134
9,625,632 B2 * 4/2017 Weichelt ............ G02B 27/0012
(Continued)

FOREIGN PATENT DOCUMENTS

| CN | 101510012 A | 8/2009 |
| CN | 102713513 A | 10/2012 |

(Continued)

OTHER PUBLICATIONS

International Search Report and Written Opinion of PCT Application No. PCT/JP2020/011448, issued on Apr. 21, 2020, 09 pages of ISRWO.

*Primary Examiner* — Trang U Tran
(74) *Attorney, Agent, or Firm* — CHIP LAW GROUP

(57) ABSTRACT

The present disclosure relates to a medical image processing system including a light source that irradiates an observation target with light; an image capturing control unit that controls capturing of an image of the observation target irradiated with the light and an endoscope including a scope having a tubular shape and made from a rigid or flexible material, a camera head including an imaging element that captures an image, and an optical element insertion unit provided between the scope and the camera head. Further, the optical element insertion unit includes two or more optical elements having the effect of extending the depth of field, and at least one of the optical elements is movable.

9 Claims, 9 Drawing Sheets

(51) Int. Cl.
  *A61B 1/04* (2006.01)
  *A61B 1/045* (2006.01)
  *G02B 5/30* (2006.01)
  *G02B 23/24* (2006.01)
  *A61B 1/06* (2006.01)
  *A61B 1/07* (2006.01)
  *H04N 23/50* (2023.01)

(52) U.S. Cl.
  CPC ....... *G02B 5/3083* (2013.01); *G02B 23/2484* (2013.01); *H04N 23/56* (2023.01); *A61B 1/0669* (2013.01); *A61B 1/07* (2013.01); *H04N 23/555* (2023.01)

(58) Field of Classification Search
  CPC . H04N 23/555; G02B 5/3083; G02B 23/2484
  USPC .......................................................... 348/68
  See application file for complete search history.

(56) References Cited

U.S. PATENT DOCUMENTS

| | | |
|---|---|---|
| 9,762,788 B2 * | 9/2017 | Komatsu ................. G02B 7/38 |
| 9,939,572 B2 | 4/2018 | Weichelt |
| 2012/0314061 A1 | 12/2012 | Yasugi |

FOREIGN PATENT DOCUMENTS

| | | | | |
|---|---|---|---|---|
| JP | 2008-245157 A | 10/2008 | | |
| JP | 2017-158764 A | 9/2017 | | |
| WO | 2012/070208 A1 | 5/2012 | | |
| WO | WO 2018/109117 A1 * | 6/2018 | ............... | A61B 1/00 |
| WO | 2019/044328 A1 | 3/2019 | | |

* cited by examiner

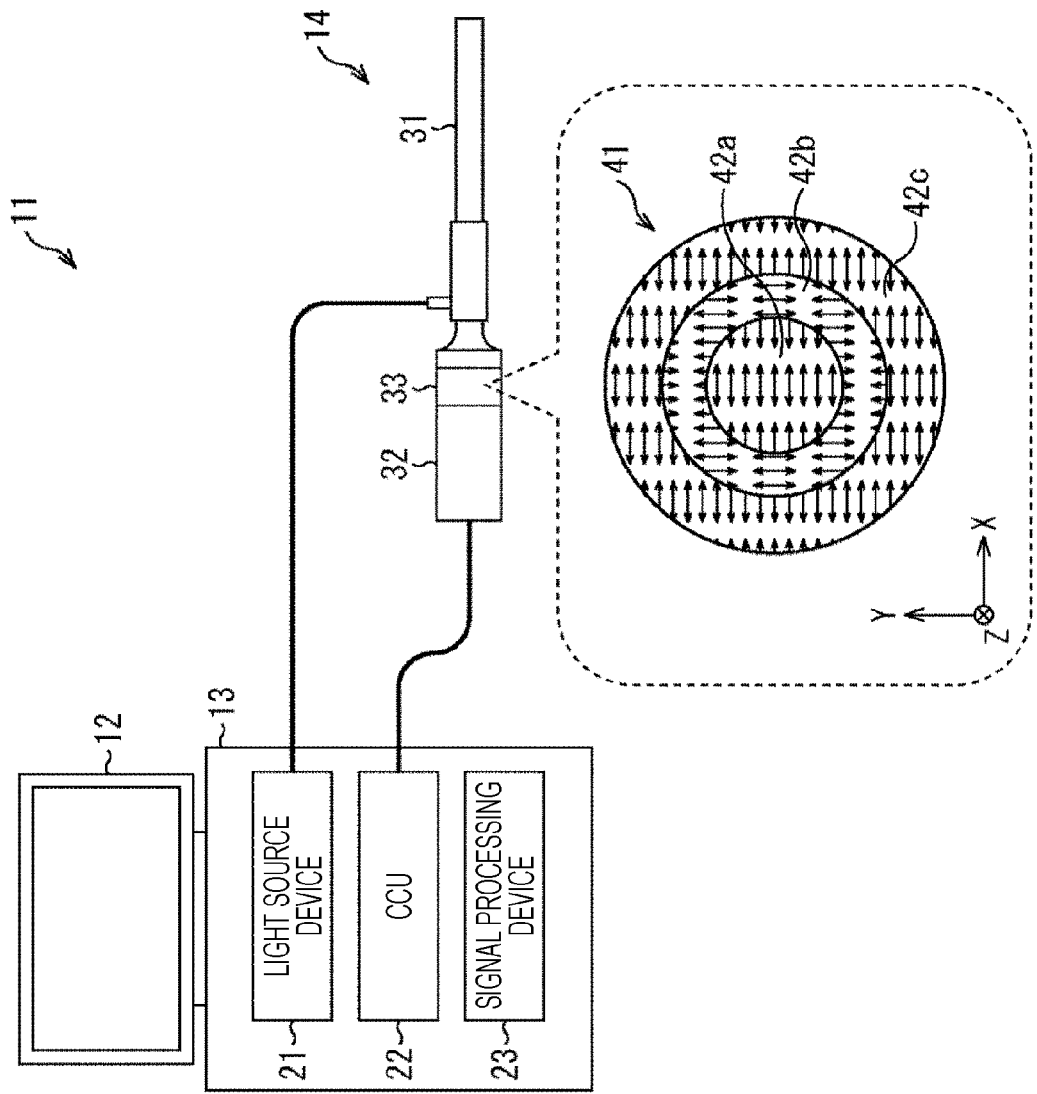

OPTICAL SYSTEM, ENDOSCOPE, AND MEDICAL IMAGE PROCESSING SYSTEM

CROSS REFERENCE TO RELATED APPLICATIONS

This application is a U.S. National Phase of International Patent Application No. PCT/JP2020/011448 filed on Mar. 16, 2020, which claims priority benefit of Japanese Patent Application No. JP 2019-063267 filed in the Japan Patent Office on Mar. 28, 2019. Each of the above-referenced applications is hereby incorporated herein by reference in its entirety.

TECHNICAL FIELD

The present disclosure relates to an optical system, an endoscope, and a medical image processing system, and more particularly relates to an optical system, an endoscope, and a medical image processing system capable of adjusting an effect of extending a depth of field.

BACKGROUND ART

Conventionally, medical observation devices such as an endoscope and a microscope generally acquire an image having a shallow depth of field. However, an operative field is deep in many cases, and there is a demand for a medical observation device having a deep depth of field.

In view of this, in order to increase the depth of field, there has been proposed an endoscope, a microscope, or the like including an extended depth of field (EDOF) optical system for extending the depth of field.

For example, an image processing device disclosed in Patent Document 1 includes an EDOF optical system including a birefringent mask and a control unit using a function for adjusting a blur amount according to a condition, and makes it possible to observe a subject image in a more suitable mode in accordance with a state, a situation, and the like regarding observation of the subject image.

CITATION LIST

Patent Document

Patent Document 1: Japanese Patent Application Laid-Open No. 2017-158764

SUMMARY OF THE INVENTION

Problems to be Solved by the Invention

In conventional EDOF optical systems, however, noise may be generated in an image or a modulation transfer function may be reduced in trade-off with extension of the depth of field. Therefore, depending on a medical scene, there is a need to, for example, increase, decrease, cause, or eliminate an effect of extending the depth of field. However, an EDOF optical system that meets such a need has not been provided.

The present disclosure has been made in view of such a situation, and an object thereof is to provide an EDOF optical system capable of adjusting an effect of extending the depth of field.

Solutions to Problems

An optical system according to one aspect of the present disclosure includes two or more optical elements having an effect of extending a depth of field, and at least one of the optical elements is movable.

An endoscope according to one aspect of the present disclosure includes: a scope having a tubular shape and made from a rigid or flexible material; and a camera head including an imaging element that captures an image, in which: the imaging element receives light having passed through an optical system including two or more optical elements having an effect of extending a depth of field; and at least one of the optical elements is movable.

A medical image processing system according to one aspect of the present disclosure includes: a light source that irradiates an observation target with light; an image capturing control unit that controls capturing of an image of the observation target irradiated with the light; and an endoscope including a scope having a tubular shape and made from a rigid or flexible material and a camera head including an imaging element that captures an image, in which: the imaging element receives light having passed through an optical system including two or more optical elements having an effect of extending a depth of field; and at least one of the optical elements is movable.

In one aspect of the present disclosure, two or more optical elements having an effect of extending a depth of field are provided, and at least one of the optical elements is movable.

BRIEF DESCRIPTION OF DRAWINGS

FIG. 1 is a block diagram illustrating a configuration example of an embodiment of a medical image processing system to which the present technology is applied.

MODE FOR CARRYING OUT THE INVENTION

Figure 2A:
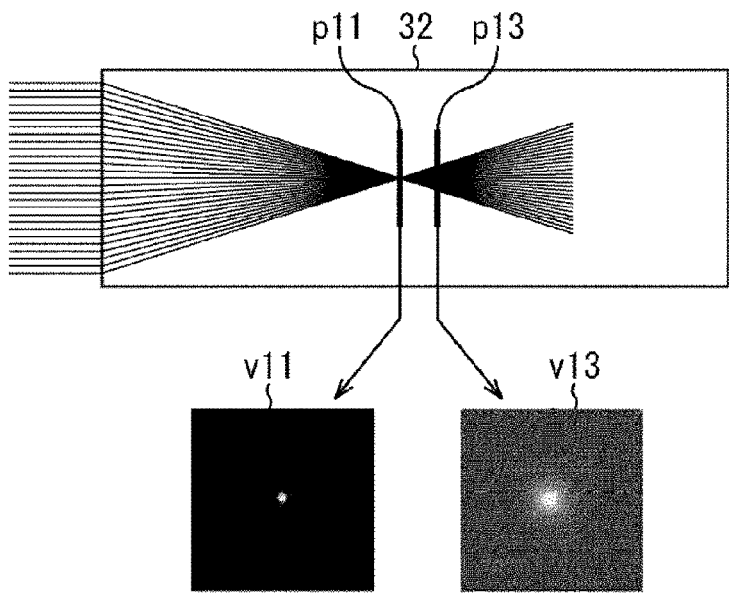
FIGS. 2A and 2B are diagrams for explaining a characteristic of a birefringent mask.

Hereinafter, specific embodiments to which the present technology is applied will be described in detail with reference to the drawings.

Configuration Example of Medical Image Processing System

FIG. 1 is a block diagram illustrating a configuration example of an embodiment of a medical image processing system to which the present technology is applied.

As illustrated in FIG. 1, a medical image processing system 11 is formed by mounting various devices for endoscopic surgery on a cart 13 on which a display device 12 is placed, and, for example, can perform image processing on an image acquired by an endoscope 14 for use in endoscopic surgery.

The display device 12 displays an image acquired by the endoscope 14, an image obtained by performing image processing on the image, and the like.

In the example of FIG. 1, a light source device 21, a camera control unit (CCU) 22, and a signal processing device 23 are mounted on the cart 13.

The light source device 21 includes, for example, an LED, a xenon lamp, a halogen lamp, a laser light source, or a light source corresponding to a combination thereof, and supplies irradiation light to be emitted toward an observation target to the endoscope 14 through a light guide.

The CCU 22 controls capturing of images by an imaging element included in a camera head 32, thereby supplying an image of the observation target captured by the imaging element.

The signal processing device 23 performs signal processing based on the image acquired by the endoscope 14, thereby performing image processing on the image. For example, as described later, the signal processing device 23 performs signal processing to which an EDOF technology using a birefringent mask is applied, thereby performing image processing for further extending a depth of field of the image captured by the imaging element of the camera head 32.

The endoscope 14 includes a lens barrel 31 and the camera head 32 and can include an optical element insertion unit 33 between the lens barrel 31 and the camera head 32. Note that, for example, it is possible to adopt not only a structure in which the optical element insertion unit 33 is detachable from both the lens barrel 31 and the camera head 32, but also a structure in which the optical element insertion unit 33 is a part of the lens barrel 31, a structure in which the optical element insertion unit 33 is a part of the camera head 32, or other structures.

The lens barrel 31 is a scope having a tubular shape and made from a rigid or flexible material, and a part of the scope having a predetermined length from a distal end thereof is inserted into a body cavity of a patient. For example, the distal end of the lens barrel 31 has an opening into which an objective lens is fitted. Further, a side surface of the lens barrel 31 has an introduction portion that introduces light generated in the light source device 21 into the lens barrel 31. The introduction portion and the light source device 21 are connected by the light guide. Then, the light introduced into the lens barrel 31 is guided to the distal end of the lens barrel 31 by the light guide extended in the lens barrel 31, and is emitted toward an observation target in the body cavity of the patient through the objective lens.

As described later with reference to FIG. 4, the camera head 32 includes an imaging element 53 that captures an image, an image forming optical system 51 that forms an image of the observation target, a diaphragm 52 that adjusts an amount of light, and the like, and captures an image under the control of the CCU 22, thereby supplying the image to the CCU 22.

The optical element insertion unit 33 provided between the lens barrel 31 and the camera head 32 is a unit into which an optical element such as a birefringent mask (BM) 41 is insertable. Note that examples of the optical element insertable into the optical element insertion unit 33 encompass a cubic phase mask. Further, a detailed configuration of the optical element insertion unit 33 will be described later with reference to FIG. 4.

For example, in the medical image processing system 11, various optical elements are interposed between the lens barrel 31 and the camera head 32 by using the optical element insertion unit 33. This makes it possible to change optical characteristics of a series of optical systems that forms a subject image on the imaging element in the camera head 32, thereby adjusting a blur amount (e.g., controlling the depth of field) of an image to be captured.

Here, there will be described a configuration of the optical element to be inserted into the optical element insertion unit 33 provided between the lens barrel 31 and the camera head 32 of the endoscope 14.

In recent years, resolution of an imaging element (so-called image sensor) for use in an imaging device such as a camera has been increased. Not only an "HD (1280×720)" imaging element but also "4K UHD (3840×2160)" and "8K UHD (7680×4320)" imaging elements have been proposed. Therefore, a medical observation device (imaging device) such as the endoscope 14 according to the present embodiment is also desired to capture a higher resolution image. Meanwhile, a pixel size of the imaging element tends to be smaller as the resolution is increased, and thus an amount of light condensed by each pixel tends to be relatively reduced. In such a situation, for example, an insufficient light amount may be compensated by further opening the diaphragm (i.e., further reducing the f-number). However, the depth of field may be further decreased as the diaphragm is opened.

In view of the above situation, for example, technologies called EDOF for extending the depth of field may be applied. Among such EDOF technologies, an EDOF technology using a birefringent mask is applied to the endoscope 14 according to the present embodiment. This makes it possible to further extend the depth of field of an image to be captured. Specifically, as described above, the endoscope 14 according to the present embodiment is provided so that an optical element is insertable into the optical element insertion unit 33 provided between the lens barrel 31 and the camera head 32, and the depth of field of the image to be captured is controlled by inserting a birefringent mask as the optical element.

For example, FIG. 1 illustrates a configuration of the birefringent mask 41 viewed from an optical axis direction of the camera head 32 as an example of the birefringent mask 41 inserted into the optical element insertion unit 33. Note that, regarding the birefringent mask 41 of FIG. 1, a horizontal direction in a part surrounded by a broken line in FIG. 1 is an x direction, a vertical direction therein is a y direction, and a depth direction therein (i.e., the optical axis direction of the camera head 32) is a z direction. Further, in the following description, the optical axis direction of the imaging element included in the camera head 32 (i.e., the depth direction) is the z direction, and the horizontal direction and the vertical direction of an image to be captured by the imaging element (i.e., the directions perpendicular to the optical axis) are the x direction and the y direction, unless otherwise defined.

In the birefringent mask 41, a plurality of polarizing elements 42 is concentrically arranged from the vicinity of the center to the outside, and three polarizing elements 42a to 42c are arranged in the example of FIG. 1. That is, in the birefringent mask 41, the three polarizing elements 42a to 42c are concentrically arranged on an xy plane perpendicular to the optical axis. Note that, in FIG. 1, arrows drawn in the birefringent mask 41 schematically indicate polarization directions of the polarizing elements 42 in which the respective arrows are drawn. That is, the polarizing elements 42a to 42c are provided so that adjacent polarizing elements have different (substantially orthogonal) polarization directions.

For example, in the example of FIG. 1, the polarization direction of the polarizing element 42a is the x direction. Meanwhile, the polarization direction of the polarizing element 42b adjacent to the polarizing element 42a is the y direction, which is a direction rotated by 90 degrees from the polarization direction (x direction) of the polarizing element 42a. Similarly, the polarization direction of the polarizing element 42c adjacent to the polarizing element 42b is the x direction, which is a direction rotated by 90 degrees from the polarization direction (y direction) of the polarizing element 42b.

With such a configuration, light condensed by the lens barrel 31 is incident on any one of the polarizing elements 42a to 42c of the birefringent mask 41 depending on a position on the xy plane perpendicular to the optical axis (z direction), and the light polarized by one of the polarizing elements 42a to 42c is incident on the camera head 32.

Here, a characteristic of the birefringent mask 41 in FIG. 1 will be described with reference to FIGS. 2A and 2B.

Figure 2B:
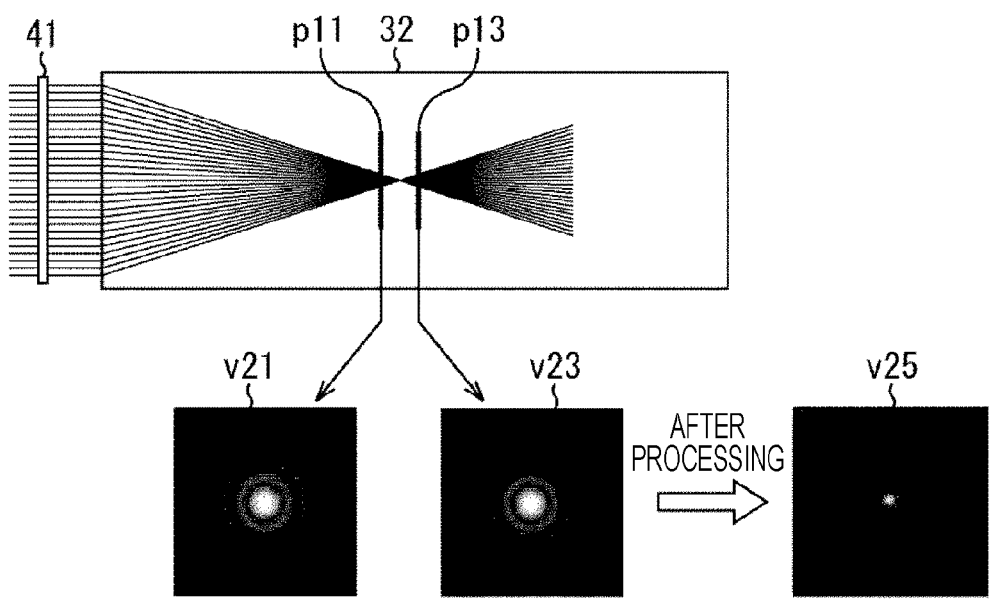

FIGS. 2A and 2B are explanatory diagrams for describing the characteristic of the birefringent mask 41 according to the present embodiment. Specifically, of FIG. 2A is an example in which the birefringent mask 41 is not interposed between the lens barrel 31 and the camera head 32, and schematically illustrates optical paths of light condensed by the lens barrel 31 to be guided to the camera head 32. Further, FIG. 2B is an example in which the birefringent mask 41 is interposed between the lens barrel 31 and the camera head 32, and schematically illustrates optical paths of light condensed by the lens barrel 31 to be guided to the camera head 32 through the birefringent mask 41.

As illustrated in FIG. 2A, the optical paths of the light condensed by the lens barrel 31 to be guided to the camera head 32 are controlled by the image forming optical system of the camera head 32 so that an image is formed on an image surface of the imaging element. In FIG. 2A, an image v11 is a schematic subject image formed at a position p11. Further, an image v13 is a schematic subject image formed at a position p13.

Meanwhile, as illustrated in FIG. 2B, the light condensed by the lens barrel 31 is guided to the camera head 32 through the birefringent mask 41, and the optical paths thereof are controlled by the image forming optical system of the camera head 32. In FIG. 2B, an image v21 is a subject image formed at the position p11. Further, an image v23 is a schematic subject image formed at the position p13.

As can be seen by comparing those images, the characteristics of the series of optical systems for forming the subject image on the imaging element of the camera head 32 (hereinafter, also simply referred to as "series of optical systems") are changed by inserting the birefringent mask 41. Specifically, in a case where the birefringent mask 41 is inserted, a shape of a formed image (i.e., point spread function (PSF)) of the subject image is less changed between the position p11 and the position p13, as compared with before the insertion of the birefringent mask 41.

Figure 3:
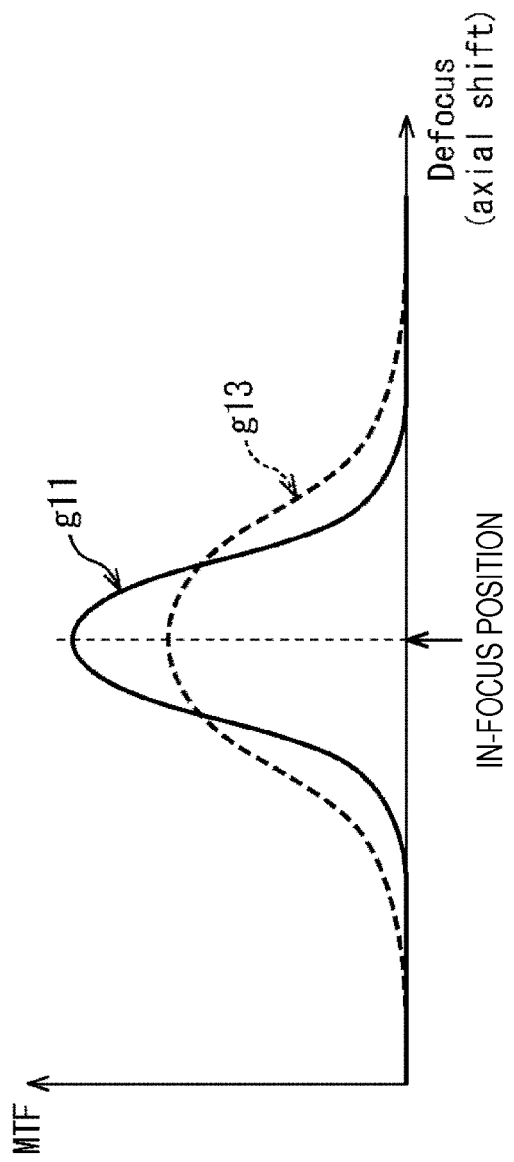
FIG. 3 illustrates an example of a change in a modulation transfer function of a series of optical systems caused by inserting a birefringent mask.

For example, FIG. 3 is an explanatory diagram for describing an example of the characteristic of the birefringent mask 41 applied to the endoscope 14 according to the present embodiment, and illustrates an example of a change in a modulation transfer function (MTF) of the series of optical systems caused by inserting the birefringent mask 41.

In FIG. 3, the horizontal axis represents a shift (i.e., defocus amount) in the optical axis direction from an image forming plane (i.e., in-focus position) of the series of optical systems, and the vertical axis represents the modulation transfer function (MTF). Further, in FIG. 3, a graph g11 shows an example of the modulation transfer function (MTF) of the series of optical systems, which is obtained in a case where the birefringent mask 41 is not interposed between the lens barrel 31 and the camera head 32 as illustrated in FIG. 2A. Further, a graph g13 shows an example of the modulation transfer function (MTF) of the series of optical systems, which is obtained in a case where the birefringent mask 41 is inserted between the lens barrel 31 and the camera head 32 as illustrated in FIG. 2B.

As illustrated in FIG. 3, in a case where the birefringent mask 41 is applied, the characteristics of the series of optical systems change such that the modulation transfer function (MTF) is distributed in a wider range in the optical axis direction, as compared with before the application of the birefringent mask 41. That is, it is possible to further extend the depth of field by applying the birefringent mask 41.

Meanwhile, as can be seen from FIG. 3, in a case where the birefringent mask 41 is applied, a value of the modulation transfer function (MTF) at the in-focus position decreases from the value thereof before the application of the birefringent mask 41. In view of this, as illustrated in FIG. 2B, the medical image processing system 1 according to the present embodiment performs restoration processing (image processing) on the image captured by the camera head 32, thereby restoring the image as to deterioration (so-called blur) of the image of the subject image caused by the decrease in the modulation transfer function (MTF). For example, in FIG. 2B, an image v25 is an example of the subject image subjected to the restoration processing, which is obtained by performing the restoration processing on the subject image v23. Note that examples of the restoration processing (e.g., processing of adjusting the blur amount) encompass processing called deconvolution. As a matter of course, the restoration processing applied to the image of the subject image is not necessarily limited to deconvolution, as long as the deterioration of the image can be restored.

With the above control, it is possible to obtain, for example, an image in which the depth of field is extended and the observation target is more clearly presented (i.e., a clearer image).

<Study on EDOF Technology Using Birefringent Mask>

A technical problem caused by applying the EDOF technology using a birefringent mask as in the medical image processing system according to the present embodiment will be described.

In a case where the depth of field is extended by a combination of the birefringent mask and the image processing (restoration processing), details of processing executed as the image processing are designed on the assumption that optical characteristics of the birefringent mask and other optical systems are known.

Here, in the EDOF technology using a birefringent mask, as described above, for example, the processing called deconvolution for removing a blur from an image captured through the optical system including the birefringent mask is applied as the image processing. In deconvolution, a blur caused by inserting the birefringent mask is removed by adaptively switching a filter coefficient of an applied filter in accordance with the optical characteristics of the optical system including the birefringent mask.

Note that examples of the deconvolution filter encompass an inverse filter and a Wiener filter. The inverse filter corresponds to, for example, a filter designed in accordance with the optical characteristics (e.g., the modulation transfer function (MTF) and the like) of the optical system including the birefringent mask (e.g., the lens barrel of the endoscope and the like). That is, the inverse filter may be designed to have, for example, an inverse characteristic of the modulation transfer function of the optical system.

Further, a spatial frequency characteristic WF of the Wiener filter is expressed by Expression (1) below.

[Expression 1]

$$WF(u, v) = \frac{H^*(u, v)}{|H(u, v)|^2 + \frac{S_n(u, v)}{S_f(u, v)}} \quad (1)$$

In Expression (1), in a case where directions horizontal to an image plane and orthogonal to each other are x and y directions, u and v represent spatial frequencies in the x and y directions, respectively. Further, H(u, v) represents an optical transfer function (OTF). Note that H*(u, v) represents a complex conjugate of H (u, v). Further, S (u, v) and Sn (u, v) represent power spectra of an original image and noise, respectively.

Meanwhile, medical devices such as a camera head and a lens barrel (e.g., a rigid scope or a flexible scope) of an endoscope for use in a medical field such as surgery are subjected to autoclave (high-pressure steam) sterilization treatment every time the medical devices are used. Therefore, in a case where, for example, the endoscope is repeatedly subjected to the autoclave sterilization treatment, optical characteristics of an optical system (i.e., the rigid scope or the flexible scope) of the endoscope, in particular, an optical characteristic of a birefringent mask may gradually change. In such a circumstance, the optical characteristic (i.e., the changed optical characteristic) of the birefringent mask may be different from an optical characteristic assumed in image signal processing, thereby affecting an image quality of an image to be output.

Specifically, examples of the optical characteristic of the birefringent mask encompass a parameter indicating a phase difference of light called retardation. Retardation is represented by a product Δnd of a refractive index difference Δn (=ne−no) and a thickness d of a birefringent substance. In a case where so-called autoclave treatment (high-pressure steam treatment) such as the autoclave sterilization treatment is performed on the birefringent mask, a change in a characteristic of the refractive index difference Δn of the birefringent mask (i.e., a decrease in the refractive index difference Δn) can be estimated. The decrease in a value of the refractive index difference Δn weakens an effect regarding extending the depth of field, for example.

As to this, in a case where, although the retardation of the birefringent mask changes as described above, image processing (restoration processing) similar to that before the retardation is changed is performed on an image captured by using the birefringent mask, it is highly possible that an image to be output has an image quality of so-called overemphasis. Therefore, in some cases, it is desirable to adaptively switch details of the image processing in accordance with the change in the retardation of the birefringent mask so as to output an image having a more suitable image quality.

Note that the optical characteristic (retardation) of the birefringent mask is measurable in a case where the birefringent mask alone is provided. However, the birefringent mask is incorporated as a part of the optical system (e.g., rigid scope) of the endoscope, the optical system of the camera head, or the like in some cases, and, in such a case, it is difficult to measure the optical characteristic of the birefringent mask alone.

Further, the restoration processing is performed on the basis of PSF information. The PSF information is acquired on the basis of a measurement result of a point spread function for an input image that is the image captured by the camera head 32. Thus, it is possible to restore the deterioration (i.e., blur) of the image of the subject image. Examples of the restoration processing encompass so-called deconvolution. As a more specific example, image processing (e.g., filter processing) based on inverse characteristics of the acquired PSF information is performed on the input image, thereby restoring the degradation (blur) of the image caused by optical characteristics indicated by the PSF information. As a matter of course, the restoration processing performed on the input image is not necessarily limited to deconvolution, as long as the deterioration of the image of the subject image can be improved on the basis of the PSF information. For example, restoration processing using machine learning or the like may be adopted.

Here, the restoration processing using machine learning can restore the deterioration of the image by, for example, performing the following learning processing. First, learning data including a pair of unrestored and restored images is prepared. Next, the learning data is input to a predetermined learning model to perform learning, thereby generating a parameter for estimating a restored image from an unrestored image. Then, an unrestored image is input to a restored image generation model tuned by using this parameter, and thus a restored image is generated. Note that the learning model and the restored image generation model are preferably a calculation model using a multilayer neural network, and more preferably a calculation model that adopts a reinforcement learning method using a multilayer neural network.

Next, configurations of the camera head 32 and the optical element insertion unit 33 will be described with reference to FIG. 4.

Figure 4:
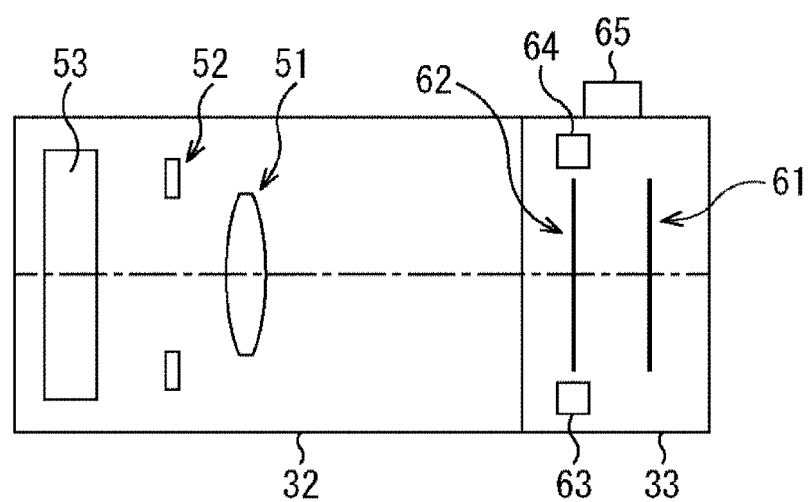
FIG. 4 illustrates a cross-sectional configuration example of a camera head and an optical element insertion unit.

As illustrated in FIG. 4, the image forming optical system 51, the diaphragm 52, and the imaging element 53 are arranged along the optical axis in the camera head 32.

In the optical element insertion unit 33, a fixed birefringent mask 61, a movable birefringent mask 62, a drive unit 63, and an angle detection unit 64 are provided. The optical element insertion unit 33 is provided with a switch 65.

In the fixed birefringent mask 61 and the movable birefringent mask 62, for example, the polarizing elements 42a to 42c similar to those of the birefringent mask 41 described with reference to FIG. 1 are arranged to form an EDOF optical system. For example, the fixed birefringent mask 61 is fixedly attached to the optical element insertion unit 33, whereas the movable birefringent mask 62 is attached to be rotatable about the optical axis in the optical element insertion unit 33.

The drive unit 63 includes a motor, a rotation transmission mechanism, and the like for rotationally driving the movable birefringent mask 62.

The angle detection unit 64 includes an encoder that detects an angle of the movable birefringent mask 62 that rotates in accordance with rotational drive by the drive unit 63. For example, the angle detected by the angle detection unit 64 is used to stop the rotational drive of the movable birefringent mask 62 at a predetermined angle such as 90 degrees or 45 degrees as described later.

The switch 65 is an operation unit operated when an instruction is made to rotationally drive the movable birefringent mask 62. For example, in response to an operation on the switch 65, the drive unit 63 can rotationally drive the movable birefringent mask 62 on the basis of the angle detected by the angle detection unit 64.

The camera head 32 and the optical element insertion unit 33 are configured as described above, and light from the observation target is incident on the camera head 32 through the EDOF optical system including the fixed birefringent mask 61 and the movable birefringent mask 62. Therefore, an image captured by the imaging element 53 can have an EDOF effect by the EDOF optical system.

<Configuration Examples of EDOF Optical System>

Configuration examples of the EDOF optical system including the fixed birefringent mask 61 and the movable birefringent mask 62 will be described with reference to FIGS. 5 to 9.

Figure 5:
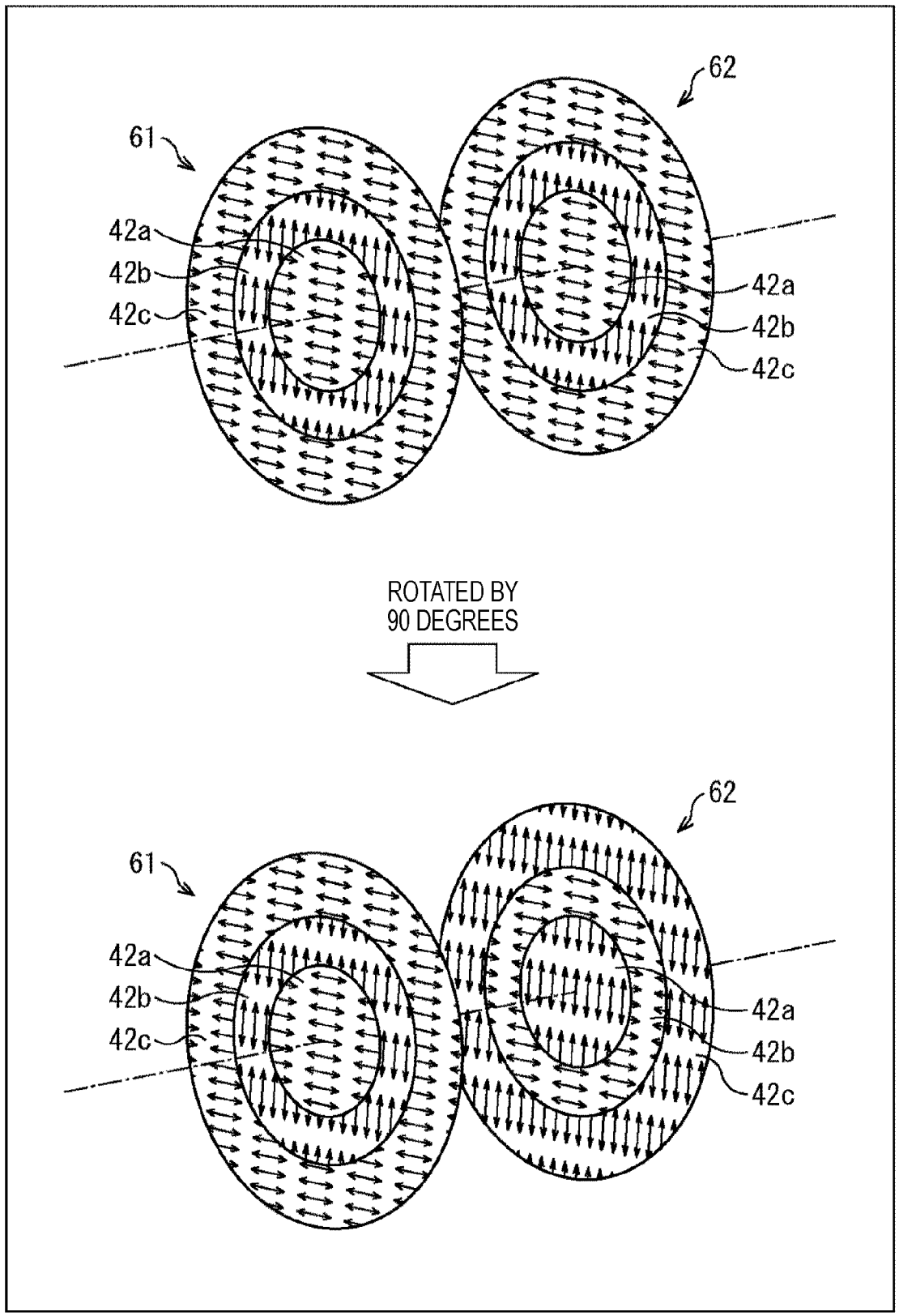
FIG. 5 illustrates a first configuration example of an EDOF optical system.

FIG. 5 illustrates a first configuration example of the EDOF optical system.

The example in an upper part of FIG. 5 shows a state in which the movable birefringent mask 62 is fixed so that the polarization directions of the polarizing elements 42a to 42c of the fixed birefringent mask 61 are the same as the polarization directions of the polarizing elements 42a to 42c of the movable birefringent mask 62. In such a state, i.e., in a case where the polarizing elements 42a to 42c of the same design are arranged to overlap each other so that the birefringent masks have a rotation angle of 0 degrees, it is possible to obtain the ordinary EDOF effect, i.e., 100% of the EDOF effect.

Then, in a case where the movable birefringent mask 62 is rotated by 90 degrees, as in the example in a lower part of FIG. 5, the polarization directions of the polarizing elements 42a to 42c of the fixed birefringent mask 61 and the polarization directions of the polarizing elements 42a to 42c of the movable birefringent mask 62 are relatively orthogonal to each other at 90 degrees. In such a state, i.e., in a case where the polarizing elements 42a to 42c of the same design are arranged to overlap each other so that the birefringent masks have a rotation angle of 90 degrees, a phase difference of light is canceled. As a result, it is possible to obtain 0% of the EDOF effect (eliminate the EDOF effect).

As described above, the EDOF optical system including the fixed birefringent mask 61 and the movable birefringent mask 62 can cause or eliminate the EDOF effect.

Further, the EDOF effect can be obtained at a desired change rate by adjusting a relative angle between the polarization directions of the polarizing elements 42a to 42c of the fixed birefringent mask 61 and the polarization directions of the polarizing elements 42a to 42c of the movable birefringent mask 62 in a range of 0 degrees and 90 degrees. That is, the EDOF effect can be increased or decreased by rotationally driving the movable birefringent mask 62 so that the movable birefringent mask 62 has an arbitrary angle.

Figure 6:
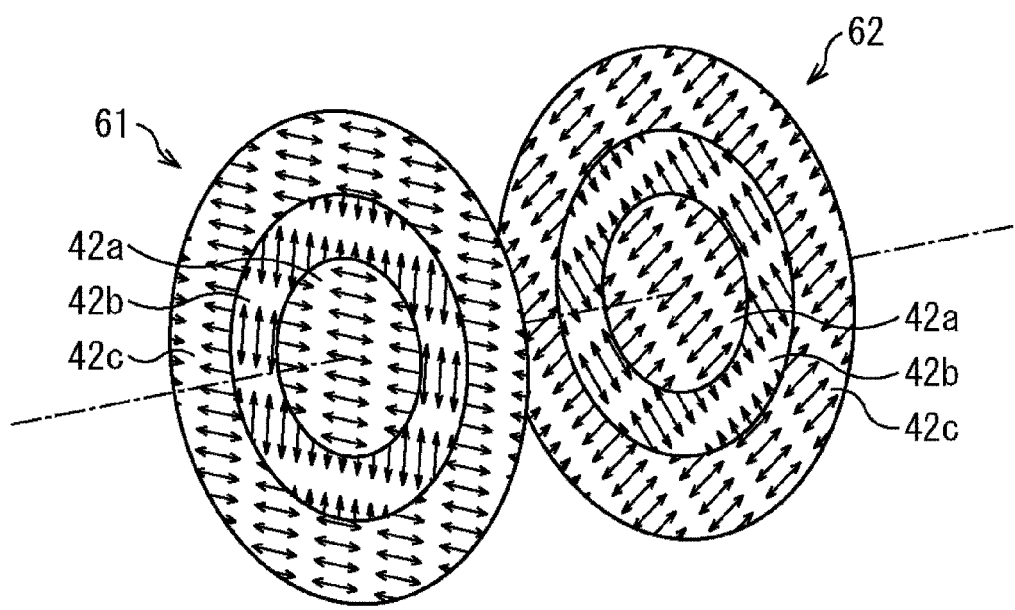
FIG. 6 illustrates a state in which a movable birefringent mask is rotated by 45 degrees.

For example, in a state in which the movable birefringent mask 62 is rotated by 45 degrees as illustrated in FIG. 6, it is possible to obtain a moderate percentage of the EDOF effect between the ordinary EDOF effect, i.e., 100% of the EDOF effect and 0% of the EDOF effect. At this time, it is not always possible to obtain 50% of the EDOF effect even in a state in which the movable birefringent mask 62 is rotated by 45 degrees, and the change rate of the characteristic can be different depending on the design of patterns of the polarizing elements 42a to 42c.

Figure 7:
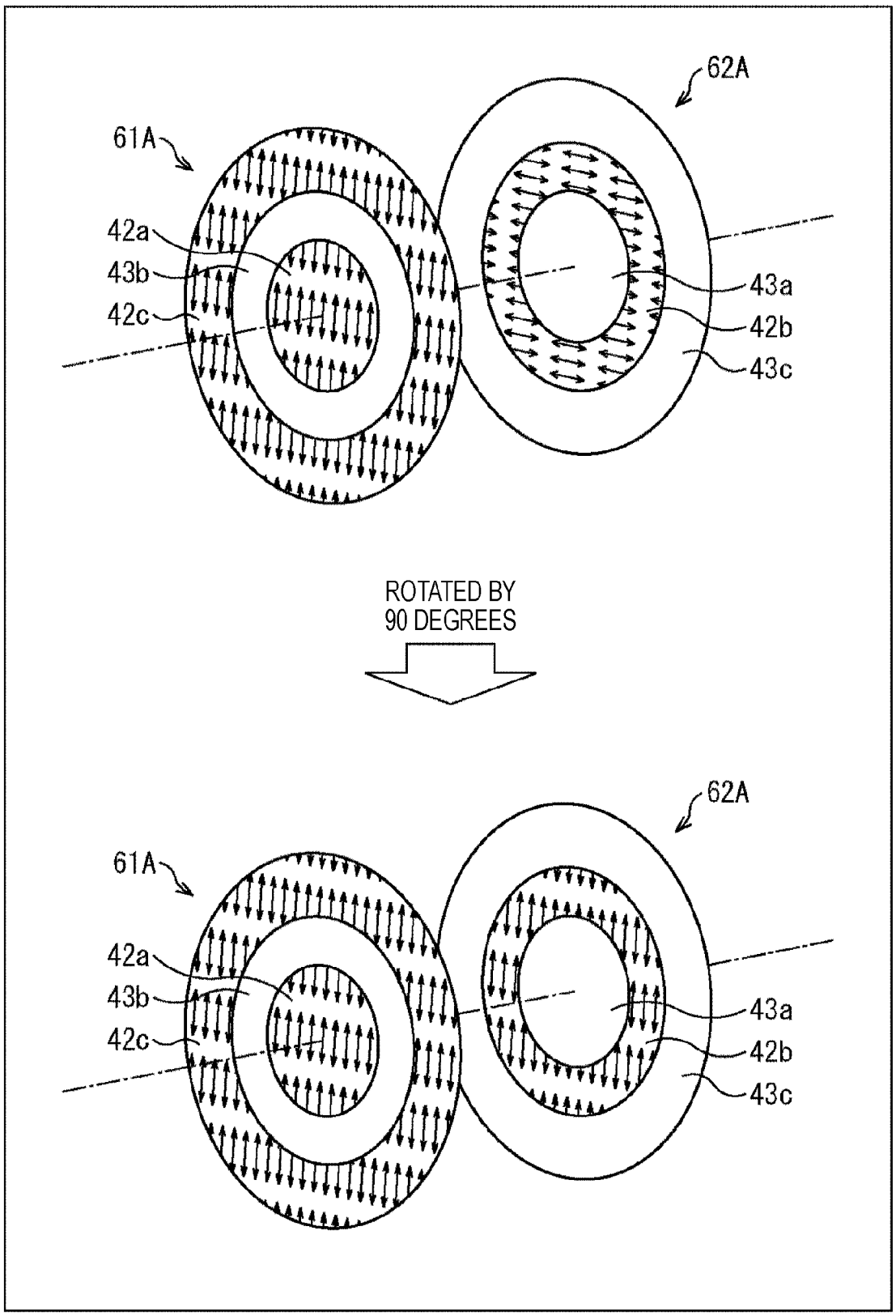
FIG. 7 illustrates a second configuration example of an EDOF optical system.

FIG. 7 illustrates a second configuration example of the EDOF optical system.

As illustrated in FIG. 7, in a fixed birefringent mask 61A, a non-polarizing element 43b having no polarization characteristic is arranged between the polarizing element 42a and the polarizing element 42c. In other words, in the fixed birefringent mask 61A, only even-numbered rings are polarizing elements and an odd-numbered ring is a non-polarizing element. For example, in the fixed birefringent mask 61A, the polarizing element 42b of the fixed birefringent mask 61 in FIG. 5 is replaced with the non-polarizing element 43b.

Further, in a movable birefringent mask 62A, the polarizing element 42b is arranged between non-polarizing elements 43a and 43c having no polarization characteristic. In other words, in the movable birefringent mask 62A, only an odd-numbered ring is a polarizing element and even-numbered rings are non-polarizing elements. For example, in the movable birefringent mask 62A, the polarizing element 42a and the polarizing element 42c of the movable birefringent mask 62 in FIG. 5 are replaced with the non-polarizing element 43a and the non-polarizing element 43c.

The example in an upper part of FIG. 7 shows a state in which the polarization directions of the polarizing elements 42a and 42c of the fixed birefringent mask 61A and the polarization direction of the polarizing element 42b of the movable birefringent mask 62A are relatively orthogonal to each other at 90 degrees. That is, in this case, the fixed birefringent mask 61A and the movable birefringent mask 62A viewed in the optical axis direction have a similar configuration to that of the birefringent mask 41 in FIG. 1, and it is possible to obtain the ordinary EDOF effect, i.e., 100% of the EDOF effect.

Then, in a case where the movable birefringent mask 62A is rotated by 90 degrees, as in the example in a lower part of FIG. 7, the polarization directions of the polarizing elements 42a and 42c of the fixed birefringent mask 61A and the polarization direction of the polarizing element 42b of the movable birefringent mask 62A coincide with each other. In such a state, all the polarization directions are aligned. As a result, it is possible to obtain 0% of the EDOF effect (eliminate the EDOF effect).

As described above, the EDOF optical system including the fixed birefringent mask 61A and the movable birefringent mask 62A can cause or eliminate the EDOF effect. Further, as described above, the EDOF effect can be obtained at a desired change rate by adjusting an angle of the movable birefringent mask 62A.

Furthermore, in a case where the EDOF optical system includes a pair of masks such as the fixed birefringent mask 61A and the movable birefringent mask 62A to, for example, halve the retardation indicating the phase difference, as compared with an EDOF optical system including only a single mask, those two masks can be as the same members. This provides, for example, a great advantage in manufacturing.

Figure 8:
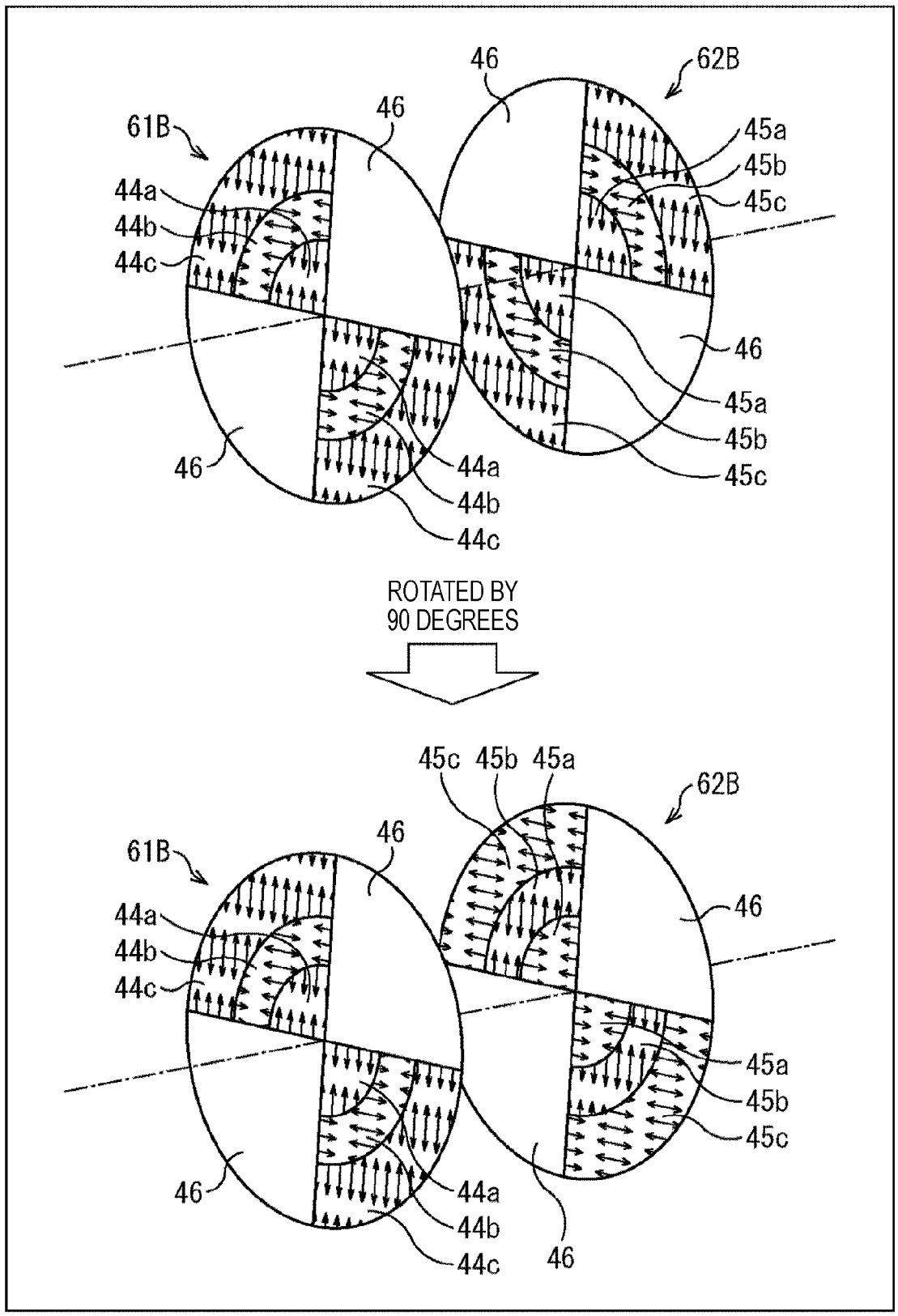
FIG. 8 illustrates a third configuration example of an EDOF optical system.

FIG. 8 illustrates a third configuration example of the EDOF optical system.

As illustrated in FIG. 8, a fixed birefringent mask 61B is divided in the form of a cross at the center thereof to have four fan shapes so that upper left and lower right fan shapes are polarizing elements 44a to 44c (polarization directions similar to those of upper left and lower right parts of the polarizing elements 42a to 42c) and upper right and lower left fan shapes are non-polarizing elements 46.

Further, a movable birefringent mask 62B is divided in the form of a cross at the center thereof to have four fan shapes so that upper right and lower left fan shapes are polarizing elements 45a to 45c (polarization directions similar to those of upper right and lower left parts of the polarizing elements 42a to 42c) and upper left and lower right fan shapes are the non-polarizing elements 46.

The example in an upper part of FIG. 8 shows a state in which polarization directions of the polarizing elements 44a to 44c of the fixed birefringent mask 61B and polarization directions of the polarizing elements 45a to 45c of the movable birefringent mask 62B coincide with each other. That is, in this case, the fixed birefringent mask 61B and the movable birefringent mask 62B viewed in the optical axis direction have a similar configuration to that of the birefringent mask 41 in FIG. 1, and it is possible to obtain the ordinary EDOF effect, i.e., 100% of the EDOF effect.

Then, in a case where the movable birefringent mask 62B is rotated by 90 degrees, as in the example in a lower part of FIG. 8, the polarization directions of the polarizing elements 44a to 44c of the fixed birefringent mask 61B and the polarization directions of the polarizing elements 45a to 45c of the movable birefringent mask 62B are relatively orthogonal to each other at 90 degrees, respectively. In such a state, the phase difference of light is canceled. As a result, it is possible to obtain 0% of the EDOF effect (eliminate the EDOF effect).

As described above, the EDOF optical system including the fixed birefringent mask 61B and the movable birefringent mask 62B can cause or eliminate the EDOF effect. Further, as described above, the EDOF effect can be obtained at a desired change rate by adjusting an angle of the movable birefringent mask 62B.

Figure 9:
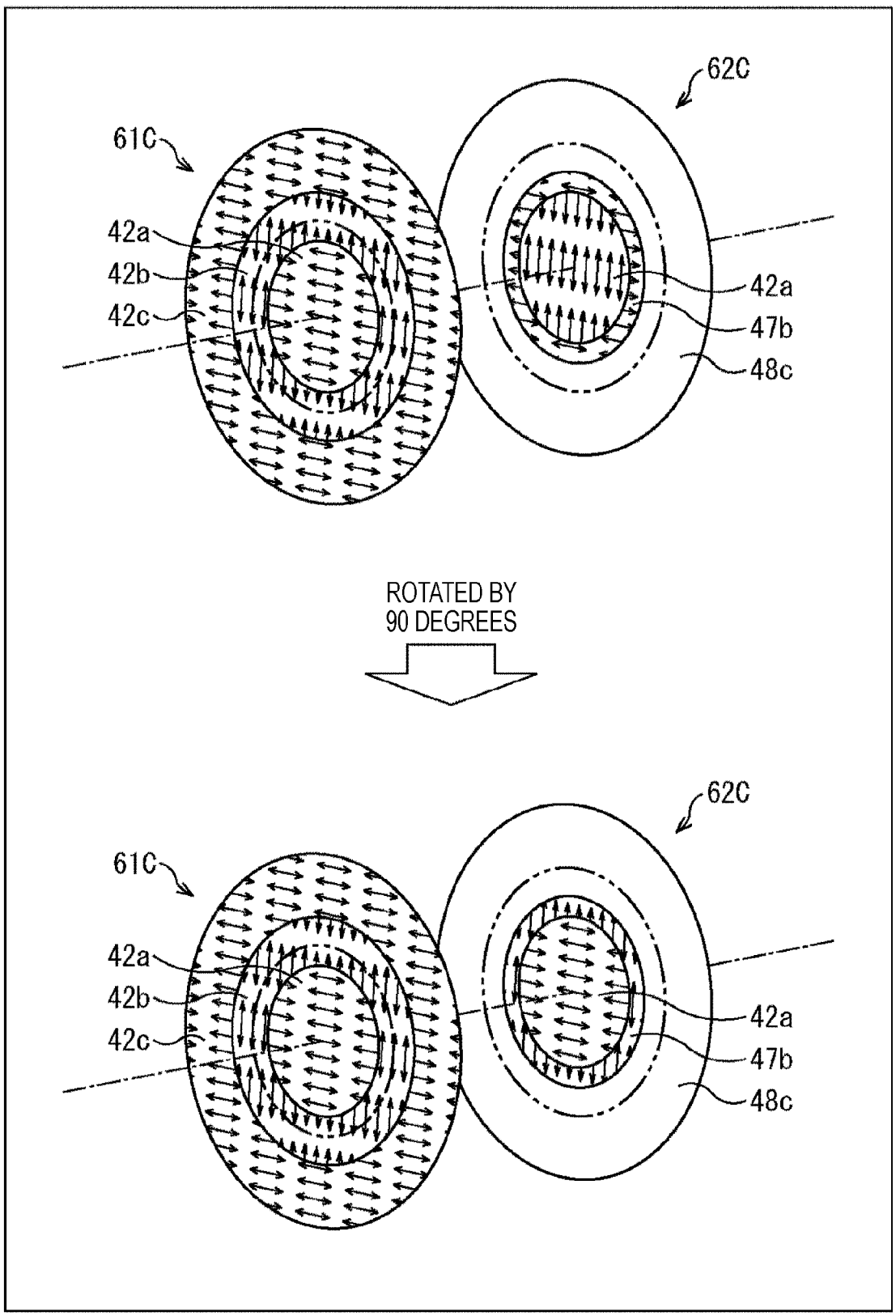
FIG. 9 illustrates a fourth configuration example of an EDOF optical system.

FIG. 9 illustrates a fourth configuration example of the EDOF optical system.

For example, FIG. 9 illustrates a configuration example where a fixed birefringent mask 61C and a movable birefringent mask 62C correspond to both two diameters (e.g., 10 mm and 4 mm) of rigid scopes.

For example, in order to obtain the EDOF effect in the two types of rigid scopes having diameters of 10 mm and 4 mm, light passes through all the ring-shaped polarizing elements provided in the birefringent mask in a case of the rigid scope having a diameter of 10 mm, whereas light passes through only limited ring-shaped polarizing elements near the center in a case of the rigid scope having a diameter of 4 mm. With such a configuration, the first fixed birefringent mask 61C has a similar configuration to that of the general birefringent mask 41 (FIG. 1), and the second movable birefringent mask 62C has a configuration in which ring-shaped polarizing elements are provided only in the vicinity of the center thereof.

That is, the polarizing elements 42a to 42c are arranged in the fixed birefringent mask 61C as in the birefringent mask 41 in FIG. 1. Meanwhile, in the movable birefringent mask 62C, the same polarizing element 42a is provided, but a polarizing element 47b has an outer shape smaller than that of the polarizing element 42b. Further, in the movable birefringent mask 62C, a non-polarizing element 48c wider than the polarizing element 42c is arranged outside the polarizing element 42b. Note that, in FIG. 9, a two-dot chain line in the fixed birefringent mask 61C indicates the outer shape of the polarizing element 47b, and a two-dot chain line in the movable birefringent mask 62C indicates the outer shape of the polarizing element 42b.

Further, the example in an upper part of FIG. 9 shows a state in which the polarization directions of the polarizing elements 42a and 42b of the fixed birefringent mask 61C and the polarization directions of the polarizing elements 42a and 47b of the movable birefringent mask 62C are relatively orthogonal to each other at 90 degrees. Therefore, in this case, the phase difference of light is canceled. As a result, it is possible to obtain 0% of the EDOF effect (eliminate the EDOF effect) in the rigid scope having a diameter of 4 mm, and obtain the EDOF effect to some extent in the rigid scope having a diameter of 10 mm.

Then, in a case where the movable birefringent mask 62B is rotated by 90 degrees, as in the example in a lower part of FIG. 9, the polarization directions of the polarizing elements 42a and 42b of the fixed birefringent mask 61C and the polarization directions of the polarizing elements 42a and 47b of the movable birefringent mask 62C coincide with each other. Therefore, in this case, the fixed birefringent mask 61C and the movable birefringent mask 62C viewed in the optical axis direction have a similar configuration to that of the birefringent mask 41 in FIG. 1, and it is possible to obtain the ordinary EDOF effect, i.e., 100% of the EDOF effect.

Note that the fixed birefringent mask 61 and the movable birefringent mask 62 included in the EDOF optical system preferably have completely the same size in consideration of ease of installation. As a matter of course, the fixed birefringent mask 61 and the movable birefringent mask 62 may have different sizes.

Further, the fixed birefringent mask 61 and the movable birefringent mask 62 are generally installed at pupil positions, and thus those two masks are installed as close as possible. Furthermore, the fixed birefringent mask 61 and the movable birefringent mask 62 are installed to overlap inside of the optical element insertion unit 33. Still further, the EDOF optical system may include one of the birefringent masks in the camera head 32 and the other in the lens barrel 31, instead of providing the optical element insertion unit 33.

In addition, the EDOF effect may, for example, be caused, eliminated, increased, or decreased by adopting a mechanism other than the rotational driving mechanism such as the movable birefringent mask 62. For example, instead of the movable birefringent mask 62, a birefringent mask having a parallel movement (shift) mechanism or a birefringent mask having a flip-up (flip) mechanism may be adopted.

In addition, the signal processing device 23 can adjust a parameter of image signal processing for causing the EDOF effect in association with the rotation angle of the movable birefringent mask 62.

Note that the rotation angle of the movable birefringent mask 62 may be changed stepwise or continuously. Further, a rotation range of the movable birefringent mask 62 may be limited from 0 degrees to 90 degrees, or may be rotated without limitation. For example, in a case where the rotation range of the movable birefringent mask 62 is limited, it is preferable to provide a lock mechanism that prevents the rotation beyond the limitation.

Further, the movable birefringent mask 62 may be rotationally driven by using a motor such as the drive unit 63 or may be manually rotated by a user.

Furthermore, even in a case where the rotation angle of the movable birefringent mask 62 is displayed and presented to the user, it is difficult for the user to intuitively recognize the EDOF effect caused by the rotation angle. Therefore, the degree of the EDOF effect may be presented to the user in association with the rotation angle of the movable birefringent mask 62. For example, the rotation angle of the movable birefringent mask 62 of 0 degrees presents a strong EDOF effect, the rotation angle of 45 degrees presents a moderate EDOF effect, the rotation angle of 60 degrees presents a weak EDOF effect, and the rotation angle of 90 degrees presents no EDOF effect.

By the way, the medical image processing system 11 can be used in the following use cases by causing or eliminating the EDOF effect.

That is, the EDOF effect can be caused or eliminated frame sequentially by controlling the rotation angle of the movable birefringent mask 62 at a high speed. Therefore, the medical image processing system 11 can alternately capture an image having the EDOF effect and an image having no EDOF effect. Then, both the images are individually displayed to allow the user to simultaneously observe presence/absence of the EDOF effect in the form of a moving image. Note that, in this case, the frame rate is reduced to about half.

Further, in a case where the user is annoyed with noise in the moving image, the medical image processing system 11 can suppress the noise by controlling the rotation angle of the movable birefringent mask 62 to weaken the EDOF effect.

Furthermore, it is possible to recognize the kind of the endoscope 14 for use in the medical image processing system 11 and control the rotation angle of the movable birefringent mask 62 in accordance with the kind thereof. Thus, in the medical image processing system 11, an appropriate EDOF effect can be selected depending on the kind of the endoscope 14. This makes it possible to make a more suitable observation.

For example, in a case where a general visible light observation is switched to a special light observation such as a fluorescence observation, the medical image processing system 11 controls the rotation angle of the movable birefringent mask 62 to control the EDOF effect, thereby providing a more suitable observation.

Further, the EDOF optical system is only required to include at least two or more birefringent masks, and, for example, may include a combination of N or more (N≥2) fixed birefringent masks 61 and at least M (N≥M≥1) movable birefringent mask 62 so as to adjust the EDOF effect.

Note that, by adopting wavefront coding filters or chromatic aberration filters as the optical elements having the EDOF effect, instead of the birefringent masks, it is possible to have a similar effect to that of the birefringent masks.

<Combination Examples of Configurations>

Note that the present technology can also have the following configurations.

(1)
An optical system including
two or more optical elements having an effect of extending a depth of field, in which
at least one of the optical elements is movable.

(2)
The optical system according to (1), in which
the optical elements are birefringent masks in each of which polarizing elements having predetermined polarization directions are arranged in combination.

(3)
The optical system according to (2), in which
the optical elements use N or more (N≥2) first birefringent masks and at least M (N≥M≥1) second birefringent mask in combination, and the second birefringent mask is movable.

(4)
The optical system according to (2) or (3), in which
the optical elements are a fixed first birefringent mask and a second birefringent mask rotatable about an optical axis, and the effect of extending the depth of field is adjusted by relatively changing polarization directions of polarizing elements of the first birefringent mask and polarization directions of polarizing elements of the second birefringent mask.

(5)
The optical system according to (4), in which:
in the first birefringent mask and the second birefringent mask, a plurality of the polarizing elements is concentrically arranged from a vicinity of a center toward an outside, and the polarization direction is rotated by 90 degrees relative to the adjacent polarization elements; and
the effect of extending the depth of field is adjusted by rotationally driving the second birefringent mask rotatable about the optical axis with respect to the fixed first birefringent mask.

(6)
The optical system according to (5), in which
the first birefringent mask includes only an even-numbered ring as the polarizing element and an odd-numbered ring as a non-polarizing element, and the second birefringent mask includes only an odd-numbered ring as the polarizing element and an even-numbered ring as the non-polarizing element.

(7)
The optical system according to (5), in which:
the first birefringent mask is divided in the form of a cross at a center of the first birefringent mask to have four fan shapes so that upper left and lower right fan shapes are polarizing elements and upper right and lower left fan shapes are non-polarizing elements, and the second birefringent mask is divided in the form of a cross at a center of the second birefringent mask to have four fan shapes so that upper right and lower left fan shapes are polarizing elements and upper left and lower right fan shapes are non-polarizing elements.

(8)
The optical system according to (5), in which a predetermined polarizing element provided in the second birefringent mask has an outer shape that is set in accordance with a diameter of a rigid scope.

(9)
The optical system according to any one of (1) to (8), in which
the optical elements are wavefront coding filters or chromatic aberration filters.

(10)
An endoscope including:
a scope having a tubular shape and made from a rigid or flexible material; and
a camera head including an imaging element that captures an image, in which:
the imaging element receives light having passed through an optical system including two or more optical elements having an effect of extending a depth of field; and
at least one of the optical elements is movable.

(11)
The endoscope according to (10), in which:
an optical element insertion unit is provided between the scope and the camera head; and the movable optical element is arranged in the optical element insertion unit.

(12)

A medical image processing system including:
a light source that irradiates an observation target with light;
an image capturing control unit that controls capturing of an image of the observation target irradiated with the light; and
an endoscope including a scope having a tubular shape and made from a rigid or flexible material and a camera head including an imaging element that captures an image, in which:
the imaging element receives light having passed through an optical system including two or more optical elements having an effect of extending a depth of field; and at least one of the optical elements is movable.

(13)

The medical image processing system according to (12), in which:
an optical element insertion unit is provided between the scope and the camera head; and
the movable optical element is arranged in the optical element insertion unit.

Note that the present embodiments are not limited to the above embodiments, and can be variously modified without departing from the gist of the present disclosure. Further, the effects described in the present specification are merely examples and are not limited, and additional effects may be obtained.

REFERENCE SIGNS LIST

11 Medical image processing system
12 Display device
13 Cart
14 Endoscope
21 Light source device
22 CCU
23 Signal processing device
31 Lens barrel
32 Camera head
33 Optical element insertion unit
41 Birefringent mask
42a to 42c
Polarizing element
51 Image forming optical system
52 Diaphragm
53 Imaging element
61 Fixed birefringent mask
62 Movable birefringent mask
63 Drive unit
64 Angle detection unit
65 Switch

The invention claimed is:

1. An optical system, comprising:
at least two optical elements having an effect of extending a depth of field, wherein
the at least two optical elements include a fixed first birefringent mask and a rotatable second birefringent mask,
the rotatable second birefringent mask is rotatable about an optical axis of the optical system,
the fixed first birefringent mask includes first polarizing elements and first non-polarizing elements,
the rotatable second birefringent mask includes second polarizing elements and second non-polarizing elements,
the fixed first birefringent mask is divided in a form of a first cross at a center of the fixed first birefringent mask to have first four fan shapes so that
a first upper left fan shape of the first four fan shapes and a second lower right fan shape of the first four fan shapes are the first polarizing elements, and
a first upper right fan shape of the first four fan shapes and a second lower left fan shape of the first four fan shapes are the first non-polarizing elements,
the rotatable second birefringent mask is divided in a form of a second cross at a center of the rotatable second birefringent mask to have second four fan shapes so that
a second upper right fan shape of the second four fan shapes and a third lower left fan shape of the second four fan shapes are the second polarizing elements, and
a second upper left fan shape of the second four fan shapes and a third lower right fan shape of the second four fan shapes are the second non-polarizing elements,
the first polarizing elements are concentric from a vicinity of the center of the fixed first birefringent mask toward an outside of the fixed first birefringent mask,
the second polarizing elements are concentric from a vicinity of the center of the rotatable second birefringent mask toward an outside of the rotatable second birefringent mask,
the rotatable second birefringent mask is rotated by 90 degrees with respect to the fixed first birefringent mask,
a polarization direction of the second polarizing elements is at 90 degrees relative to a polarization direction of the first polarization elements after the rotation, and
the effect of extending the depth of field is adjustable based on the rotation of the rotatable second birefringent mask.

2. The optical system according to claim 1, further comprising a plurality of optical elements, wherein
the plurality of optical elements includes a number of fixed first birefringent masks and a number of rotatable second birefringent masks,
the plurality of optical elements includes the at least two optical elements,
the number of the fixed first birefringent masks includes the fixed first birefringent mask,
the number of the rotatable second birefringent masks includes the rotatable second birefringent mask, and
the number of the rotatable second birefringent masks is one of less than or equal to the number of the fixed first birefringent masks.

3. The optical system according to claim 1, wherein
the fixed first birefringent mask includes an even-numbered ring as a first polarizing element of the first polarizing elements and an odd-numbered ring as a first non-polarizing element of the first non-polarizing elements, and
the rotatable second birefringent mask includes an odd-numbered ring as a second polarizing element of the second polarizing elements and an even-numbered ring as a second non-polarizing element of the second non-polarizing elements.

4. The optical system according to claim 1, wherein a specific polarizing element of the second polarizing elements in the rotatable second birefringent mask has an outer shape that is set based on a diameter of a rigid scope.

5. The optical system according to claim 1, wherein the at least two optical elements are one of wavefront coding filters or chromatic aberration filters.

6. An endoscope, comprising:
a scope having a tubular shape and made from one of a rigid material or a flexible material; and
a camera head including an imaging element configured to capture an image, wherein
the imaging element is further configured to receive light having passed through an optical system including at least two optical elements,
the at least two optical elements having an effect of extending a depth of field,
the at least two optical elements include a fixed first birefringent mask and a rotatable second birefringent mask,
the rotatable second birefringent mask is rotatable about an optical axis of the optical system,
the fixed first birefringent mask includes first polarizing elements and first non-polarizing elements,
the rotatable second birefringent mask includes second polarizing elements and second non-polarizing elements,
the fixed first birefringent mask is divided in a form of a first cross at a center of the fixed first birefringent mask to have first four fan shapes so that
a first upper left fan shape of the first four fan shapes and a second lower right fan shape of the first four fan shapes are the first polarizing elements, and
a first upper right fan shape of the first four fan shapes and a second lower left fan shape of the first four fan shapes are the first non-polarizing elements,
the rotatable second birefringent mask is divided in a form of a second cross at a center of the rotatable second birefringent mask to have second four fan shapes so that
a second upper right fan shape of the second four fan shapes and a third lower left fan shape of the second four fan shapes are the second polarizing elements, and
a second upper left fan shape of the second four fan shapes and a third lower right fan shape of the second four fan shapes are the second non-polarizing elements,
the first polarizing elements are concentric from a vicinity of the center of the fixed first birefringent mask toward an outside of the fixed first birefringent mask,
the second polarizing elements are concentric from a vicinity of the center of the rotatable second birefringent mask toward an outside of the rotatable second birefringent mask,
the rotatable second birefringent mask is rotated by 90 degrees with respect to the fixed first birefringent mask, a polarization direction of the second polarizing elements is at 90 degrees relative to a polarization direction of the first polarization elements after the rotation, and
the effect of extending the depth of field is adjustable based on the rotation of the rotatable second birefringent mask.

7. The endoscope according to claim 6, further comprising an optical element insertion unit between the scope and the camera head, wherein the rotatable second birefringent mask is in the optical element insertion unit.

8. A medical image processing system, comprising:
a light source configured to irradiate an observation target with light;
an image capturing control unit configured to control capture of an image of the observation target irradiated with the light; and
an endoscope including: a scope having a tubular shape and made from one of a rigid material or a flexible material, and a camera head including an imaging element configured to capture an image, wherein
the imaging element is further configured to receive light having passed through an optical system including at least two optical elements,
the at least two optical elements having an effect of extending a depth of field,
the at least two optical elements include a fixed first birefringent mask and a rotatable second birefringent mask,
the rotatable second birefringent mask is rotatable about an optical axis of the optical system,
the fixed first birefringent mask includes first polarizing elements and first non-polarizing elements,
the rotatable second birefringent mask includes second polarizing elements and second non-polarizing elements,
the fixed first birefringent mask is divided in a form of a first cross at a center of the fixed first birefringent mask to have first four fan shapes so that
a first upper left fan shape of the first four fan shapes and a second lower right fan shape of the first four fan shapes are the first polarizing elements, and
a first upper right fan shape of the first four fan shapes and a second lower left fan shape of the first four fan shapes are the first non-polarizing elements,
the rotatable second birefringent mask is divided in a form of a second cross at a center of the rotatable second birefringent mask to have second four fan shapes so that
a second upper right fan shape of the second four fan shapes and a third lower left fan shape of the second four fan shapes are the second polarizing elements, and
a second upper left fan shape of the second four fan shapes and a third lower right fan shape of the second four fan shapes are the second non-polarizing elements,
the first polarizing elements are concentric from a vicinity of the center of the fixed first birefringent mask toward an outside of the fixed first birefringent mask,
the second polarizing elements are concentric from a vicinity of the center of the rotatable second birefringent mask toward an outside of the rotatable second birefringent mask, the rotatable second birefringent mask is rotated by 90 degrees with respect to the fixed first birefringent mask, a polarization direction of the second polarizing elements is at 90 degrees relative to a polarization direction of the first polarization elements after the rotation, and the effect of extending the depth of field is adjustable based on the rotation of the rotatable second birefringent mask.

9. The medical image processing system according to claim 8, further comprising an optical element insertion unit between the scope and the camera head, wherein the rotatable second birefringent mask is in the optical element insertion unit.

* * * * *